E

(12) United States Patent
Wasan et al.

(10) Patent No.: US 10,835,489 B2
(45) Date of Patent: Nov. 17, 2020

(54) MODIFIED RELEASE FORMULATIONS OF MYCOPHENOLATE MOFETIL

(71) Applicant: University of Saskatchewan, Saskatoon (CA)

(72) Inventors: Ellen K. Wasan, Saskatoon (CA); Ahmed Shoker, Saskatoon (CA); Holly G. Mansell, Saskatoon (CA); Kishor M. Wasan, Saskatoon (CA)

(73) Assignee: University of Saskatchewan, Saskatoon (CA)

(*) Notice: Subject to any disclaimer, the term of this patent is extended or adjusted under 35 U.S.C. 154(b) by 0 days.

(21) Appl. No.: 16/291,269

(22) Filed: Mar. 4, 2019

(65) Prior Publication Data

US 2019/0274950 A1  Sep. 12, 2019

Related U.S. Application Data

(60) Provisional application No. 62/640,867, filed on Mar. 9, 2018.

(51) Int. Cl.
| | |
|---|---|
| *A61K 9/00* | (2006.01) |
| *A61K 9/51* | (2006.01) |
| *A61K 31/5377* | (2006.01) |
| *A61P 37/06* | (2006.01) |

(52) U.S. Cl.
CPC .......... *A61K 9/006* (2013.01); *A61K 9/5153* (2013.01); *A61K 9/5161* (2013.01); *A61K 9/5192* (2013.01); *A61K 31/5377* (2013.01); *A61P 37/06* (2018.01)

(58) Field of Classification Search
None
See application file for complete search history.

(56) References Cited

U.S. PATENT DOCUMENTS

| | | | | |
|---|---|---|---|---|
| 4,753,935 | A * | 6/1988 | Nelson | C07D 307/88 514/233.5 |
| 8,268,352 | B2 | 9/2012 | Vaya et al. | |
| 8,323,698 | B2 * | 12/2012 | Gu | A61K 9/5153 424/489 |
| 8,361,509 | B2 | 1/2013 | Lopez-Belmonte Encina et al. | |
| 8,673,359 | B2 | 3/2014 | Cho et al. | |
| 8,778,396 | B2 | 7/2014 | Pillay et al. | |
| 9,114,071 | B2 | 8/2015 | Coulter | |
| 9,492,400 | B2 * | 11/2016 | Jon | A61K 38/28 |
| 9,642,808 | B2 | 5/2017 | Jain et al. | |
| 2009/0220611 | A1 | 9/2009 | Dargelas et al. | |
| 2010/0056493 | A1 | 3/2010 | Jain et al. | |
| 2010/0159001 | A1 | 6/2010 | Cardinal et al. | |
| 2011/0008426 | A1 | 1/2011 | Jain et al. | |
| 2012/0201800 | A1 | 8/2012 | Higuchi et al. | |
| 2014/0154328 | A1 | 6/2014 | Sovic Brkicic et al. | |
| 2015/0133454 | A1 | 5/2015 | Choy et al. | |
| 2015/0202321 | A1 | 7/2015 | Alam et al. | |
| 2016/0338971 | A1 | 11/2016 | Mousa et al. | |

FOREIGN PATENT DOCUMENTS

| | | |
|---|---|---|
| IN | 783/DEL/2007 | 2/2009 |
| IN | 288448 A1 | 8/2009 |
| IN | 3602CHE2012 A | 3/2014 |
| KR | 1020110091252 A | 9/2012 |
| WO | 2006088473 A2 | 8/2006 |
| WO | 2008122993 A1 | 10/2008 |
| WO | 2014167442 A1 | 10/2014 |

OTHER PUBLICATIONS

Chitosan product info from millipore sigma. Downloaded Jan. 30, 2020 from https://www.sigmaaldrich.com/catalog/product/aldrich/448877?lang=en&region=US (Year: 2020).*
Polylactide product info from millipore sigma. Downloaded Jan. 30, 2020 from https://www.sigmaaldrich.com/materials-science/material-science-products.html?TablePage=112226945 (Year: 2020).*
A. Babu, et al. Chitosan Coated Polylactic Acid Nanoparticle-Mediated Combinatorial Delivery of Cisplatin and siRNA/Plasmid DNA Chemosensitizes Cisplatin-Resistant Human Ovarian Cancer Cells. Mol. Pharmaceutics 2014, 11, 2720-2733. (Year: 2014).*
D. Quintanar-Guerrero, H. Fessi, E. Allemann, E. Doelker. Influence of stabilizing agents and preparative variables on the formation of poly(D,L-lactic acid) nanoparticles by an emulsification-diffusion technique. International Journal of Pharmaceutics 143 (1996) 133-141). (Year: 1996).*
Google Scholar Search: influence of polyvinyl alcohol_Feb. 3, 2020 (Year: 2020).*
Google search: robert langer mucoadhesive coated nanoparticles-Jan. 30, 2020 (Year: 2020).*
M.A. Mohammed, Development of Once Daily Mycophenolate Mofetil (MMF) Sustained Release Oral Nanoparticles, Thesis University of Saskatchewan, Oct. 2018, pp. 1-105.
M. A. Mohammed et al., An Overview of Chitosan Nanoparticles and Its Application in Non-Parenteral Drug Delivery, Pharmaceutics, vol. 9 (53), Nov. 20, 2017, pp. 1-26.
Y. Wang et al., Chitosan-Modified PLGA Nanoparticles with Versatile Surface for Improved Drug Delivery, AAPS PharmSciTech, vol. 14, No. 2, Jun. 2, 2013, pp. 585-592.
J. Pandit et al., Chitosan Coated PLGA Nanoparticles of Bevacizumab as Novel Drug Delivery to Target Retina Optimization Characterization and In Vitro Toxicity Evaluation, Artificial Cells, Nanomedicine, and Biotechnology, vol. 45, No. 7, Nov. 16, 2016, pp. 1397-1407.
Chronopoulu, L. et al. Chitosan-coated PLGA nanoparticles: A sustained drug release strategy for cell cultures, Colloids and Surfaces B. Biointerfaces, 2013, 103 pp. 310-317.
Yuancai, D. (2016) Chitosan-coated PLGA Nanoparticles for Oral Administration of Paclitaxel, in Nanoparticles of a biodegradable polymers for clinical administration of paclitaxel, Thesis, National University of Singapore; pp. 88-108.

(Continued)

*Primary Examiner* — Michael P Cohen
(74) *Attorney, Agent, or Firm* — Bereskin & Parr LLP/S.E.N.C.R.L., s.r.l.; Patricia Folkins

(57) ABSTRACT

The present application discloses modified release mucoadhesive formulations of mycophenolate mofetil and pharmaceutical compositions thereof useful in the treatment of, for example, post-transplant organ rejection. Method of preparing the formulations is also disclosed.

28 Claims, 8 Drawing Sheets

(56) References Cited

OTHER PUBLICATIONS

Figure 1:
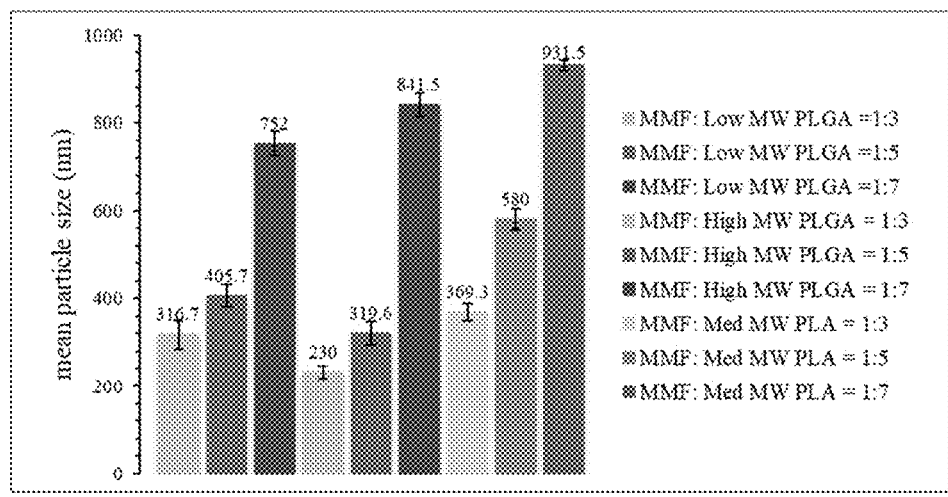

Singh, P.K. et al. Macrophage-targeted chitosan anchored PLGA nanoparticles bearing doxorubicin and amphotericin B against visceral leishmaniasis, RSC Advances, 2016, 6, pp. 71707-71718.
Nafee, N. et al. Chitosan-coated PLGA nanoparticles for DNA/RNA delivery: Effect of the formulation parameters on complexation and transfection of antisense oligonucleotides, Nanomedicine: nanotechnology, biology and medicine, 2007 3(3), pp. 173-183.
Guo, M. et al. Mechanisms of chitosan-coated poly(lactic-co-glycolic acid) nanoparticles for improving oral absorption of 7-ethyl-10-hydroxycamptothecin, Nanotechnology, 2013, 24, pp. 245101.
Yuan, X.B. et al. Preparation of rapamycin-loaded chitosan/PLA nanoparticles for immunosuppression in corneal transplantation, Int. J. Pharm, 2008, 12 pp. 241-248.
Nagarwal, R.C. et al. Chitosan coated PLA nanoparticles for ophthalmic delivery: characterization, in-vitro and in-vivo study in rabbit eye, J Biomed Nanotechnology, 2010, 6(6) pp. 648-657.
Dev A., et al. Preparation of poly(lactic acid)/chitosan nanoparticles for anti-HIV drug delivery applications, Carbohydrate Polymers, 2010, 80: 833-838.
Chen, H. et al. Chitosan Surface-Modified PLGA Nanoparticles: Preparation, Characterization, and Evaluation of their In Vitro Drug-Release Behaviors and Cytotoxicities, Current Nanoscience, 2014, 10(2):255-262 (Abstract only).

\* cited by examiner

MODIFIED RELEASE FORMULATIONS OF MYCOPHENOLATE MOFETIL

This application claims the benefit of Provisional Application Ser. No. 62/640,867, filed Mar. 9, 2018, which is hereby incorporated herein by reference

FIELD

The present application relates to modified release pharmaceutical compositions. More specifically, the application relates to modified release formulations of mycophenolate mofetil and uses thereof.

BACKGROUND

Organ transplantation is the surgical replacement of a failing or diseased organ with a healthier donor organ. According to Statistics Canada, in 2014: 2356 organs were transplanted, over 4500 patients were waiting for a donor, and 278 people died while waiting for an organ. Patients after organ transplantation are generally prescribed immunosuppressive drugs for life. Every day on average, a transplant patient takes 11 pills that include immunosuppressive and other supportive drugs (Ponticelli et al. 2010). This is a burden on patients, and missing doses can lead to many outcomes such as graft impairment, increased mortality and increased healthcare costs (Dew et al. 2007).

Mycophenolate mofetil (MMF), an ester pro-drug of mycophenolic acid (MPA), is an antiproliferative immunosuppressant drug. MMF rapidly converts to MPA after administration to a subject and acts by inhibiting the proliferation of B- and T-lymphocytes by restricting inosine monophosphate dehydrogenase, which is involved in the biosynthesis of guanine nucleotides essential for lymphocyte expansion (He et al. 2011). MMF is converted to MPA by carboxylesterases in the liver and in the intestinal wall (Fujiyama et al. 2010). As MPA is also rapidly excreted from the body, a high oral dose (2 g/day) is necessary, leading to gastrointestinal toxicity (Parfitt et al. 2008). Because of this, patients take 3-4 doses/day and the side effects force the patients to stop the therapy leading to increased risks of organ rejection.

Biodegradable and biocompatible polymers such as poly (lactic-co-glycolic) acid (PLGA) (Kumari et al. 2010), poly (lactic) acid (PLA) (Palacio et al. 2016), polycaprolactone, and biocompatible polymers such as chitosan (Mohammed et al. 2017) are mostly exploited in nanoparticle drug delivery. Coating of PLGA or PLA nanoparticles with chitosan [Chakravarthi et al. 2011, Vila et al. 2002, Cho et al., U.S. Pat. No. 8,673,359, Chronopoulu et al. 2013, Wang et al. 2013, Pandit et al, 2017, Chen et al. 2014, Yuancani 2006, Singh et al. 2016, Nafee et al. 2007, Guo et al. 2013, Yuan et al. 2008, Nagarwal et al. 2010, Dev et al. 2010] has helped in achieving mucoadhesive nanoparticles for sustained delivery.

Modified release MMF formulations have been attempted [Park, KR1020110091252A], but these have not involved nanoparticle delivery.

SUMMARY

The present application includes new modified mucoadhesive nanoparticle formulations of mycophenolate mofetil for oral use. The application includes compositions that comprise mycophenolate mofetil encapsulated in PLA polymeric nanoparticles (PNPs). The PNPs are coated with chitosan (CS-PNPs) which imparts mucoadhesive properties and modulates the release properties. The nanoparticles were prepared using an emulsion solvent evaporation method.

Accordingly, the present application includes a modified release formulation for oral delivery of mycophenolate mofetil comprising polymeric nanoparticles coated with a mucoadhesive polymer, wherein the nanoparticles comprise MMF encapsulated in poly(lactic) acid.

The present application also includes a method of treating a subject with a disease, disorder, or condition that benefits from treatment with MMF comprising administering a modified release formulation of the application to the subject.

In another embodiment, for example, the disease, disorder, or condition is organ rejection.

The present application also includes a method of preparing a modified release formulation of mycophenolate mofetil for oral delivery, the method comprising:
a) adding a first solution comprising mycophenolate mofetil and PLA in an organic solvent to an aqueous solution comprising a surfactant under conditions to form a nanoparticle solution; and
b) adding the nanoparticle solution to a second solution comprising a mucoadhesive polymer and the surfactant, in an aqueous solvent and stirring to form nanoparticles coated with the mucoadhesive polymer.

Other features and advantages of the present application will become apparent from the following detailed description. However, it should be understood that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which:

FIG. 1 shows particle size of exemplary and comparative PNPs made with MMF and PLGA/PLA. Data represented as mean±SD. Legend entries represent bars from left to right.

Figure 2:
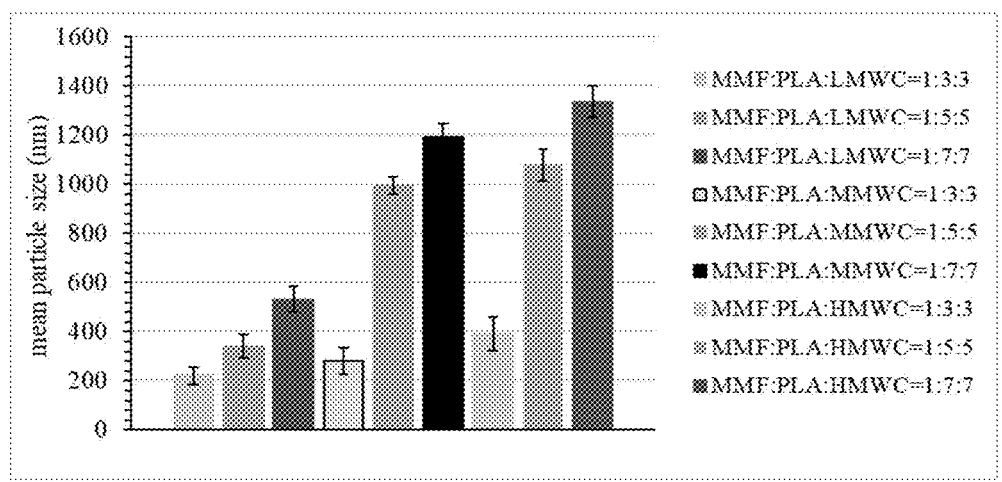

FIG. 2 shows particle size of exemplary CS-PNPs made with MMF, PLA and low, medium, and high molecular weight chitosan. Data represented as mean±SD. Legend entries represent bars from left to right.

Figure 3:
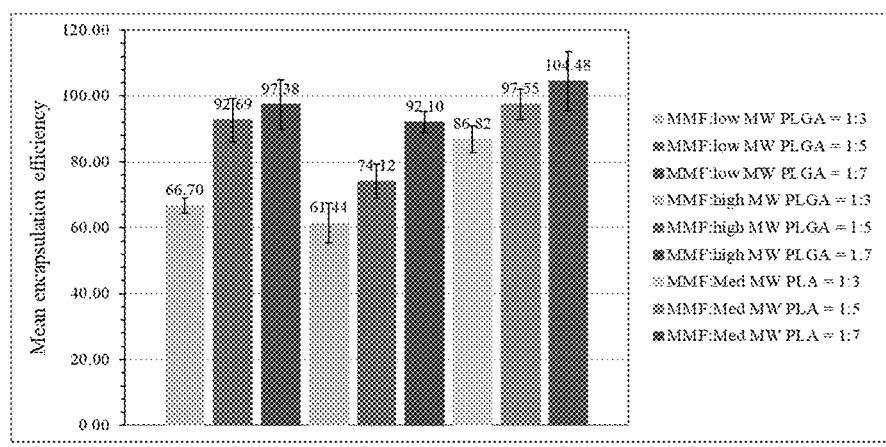

FIG. 3 shows encapsulation efficiency of PNPs made with MMF and low and high molecular weight PLGA (comparative), and medium molecular weight PLA (exemplary). Data represented as mean±SD. Legend entries represent bars from left to right.

Figure 4:
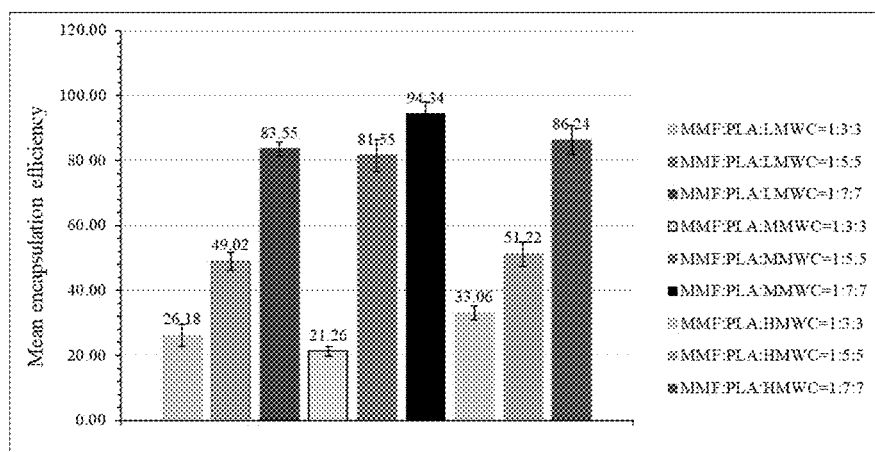

FIG. 4 shows encapsulation efficiency of exemplary CS-PNPs made with MMF, PLA and low, medium, and high molecular weight chitosan. Data represented as mean±SD. Legend entries represent bars from left to right.

Figure 5:
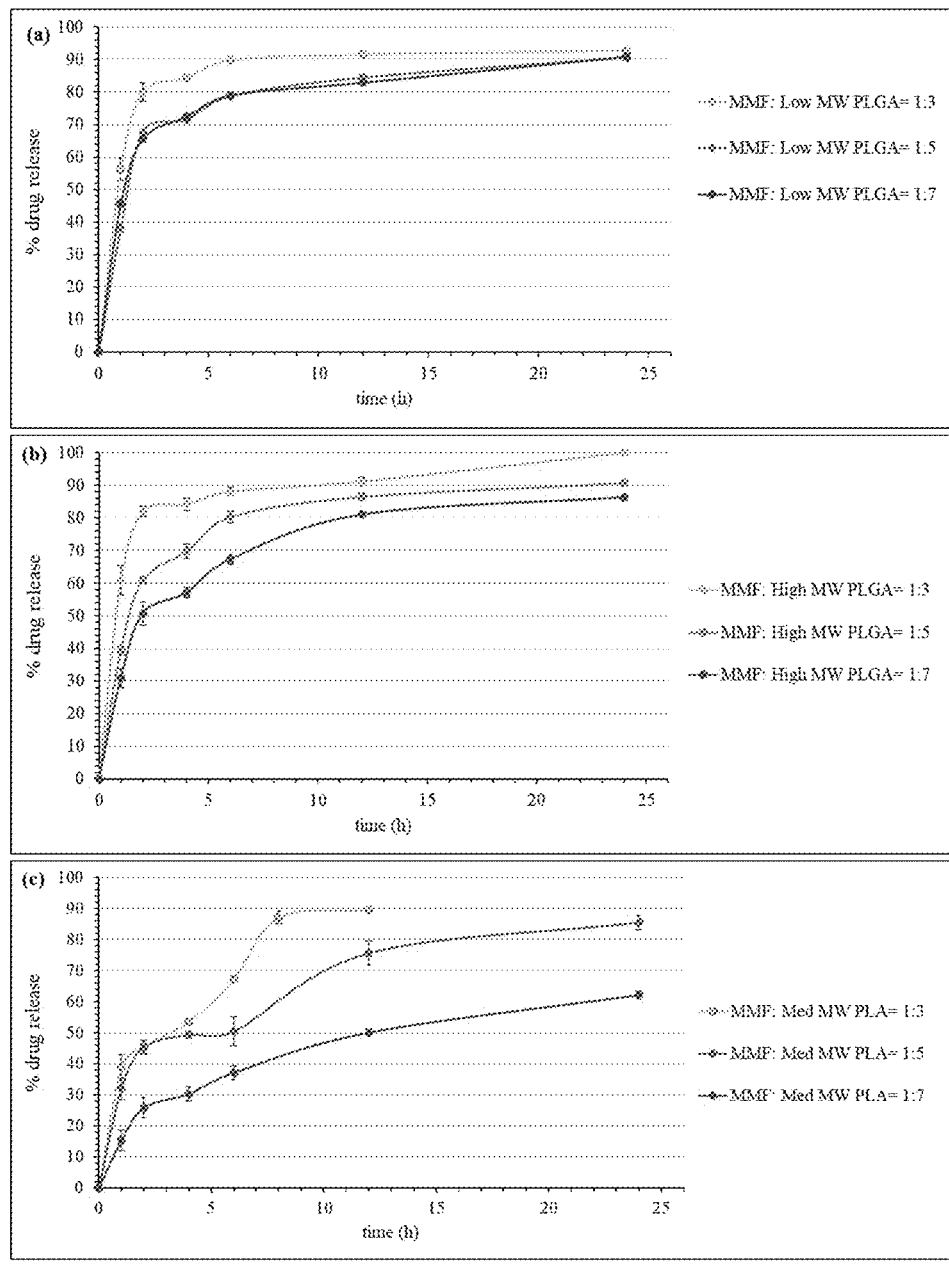

FIG. 5 contains graphs showing in vitro drug release of PNPs made with MMF and (a) low molecular weight PLGA (comparative); (b) high molecular weight PLGA (comparative); and (c) medium molecular weight PLA (exemplary). Data represented as mean±SD.

Figure 6:
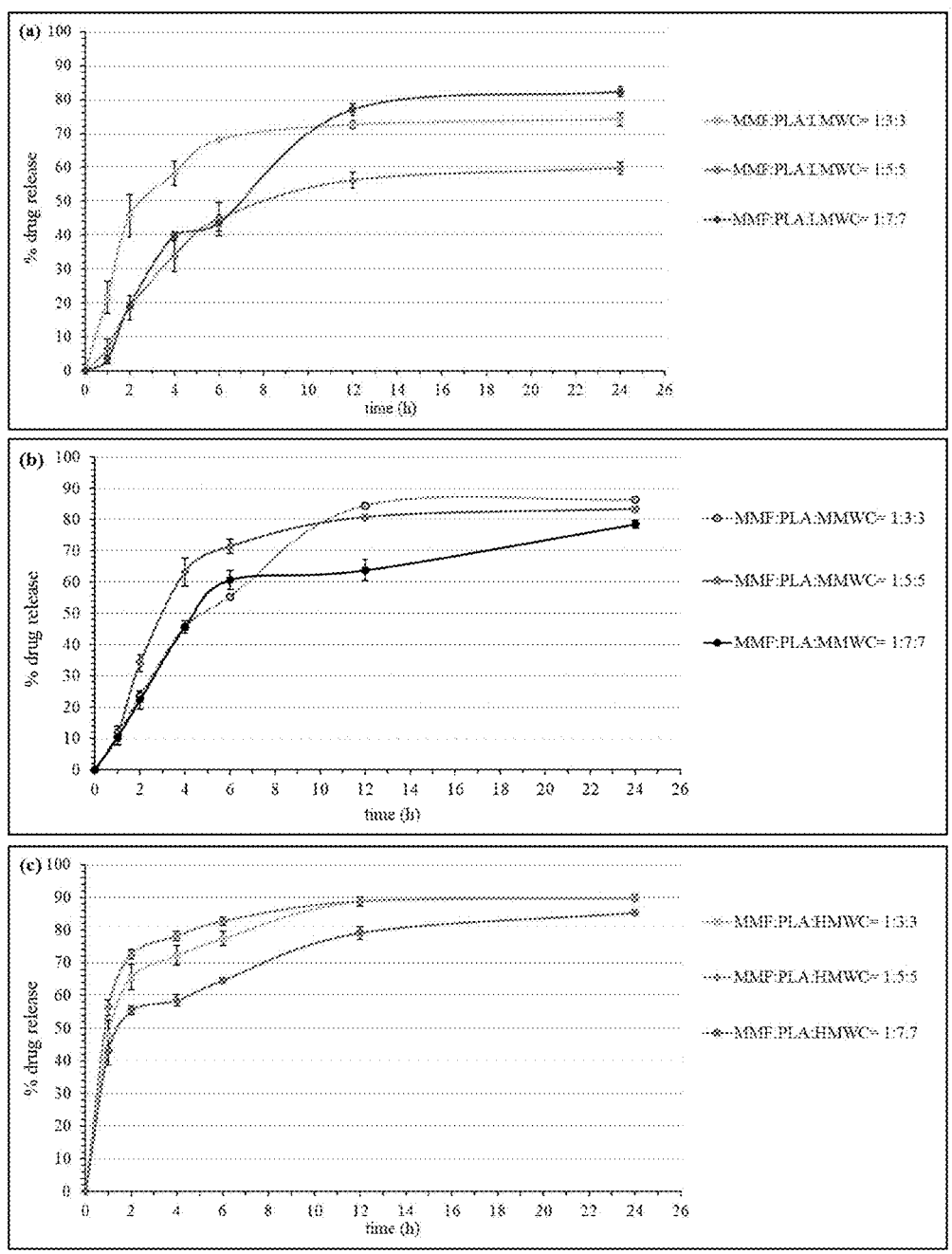

FIG. 6 shows in vitro drug release of exemplary CS-PNPs made with (a) MMF, PLA, and low molecular weight chitosan, (b) MMF, PLA, and medium molecular weight chitosan; and (c) MMF, PLA, and high molecular weight chitosan. Data represented as mean±SD.

Figure 7:
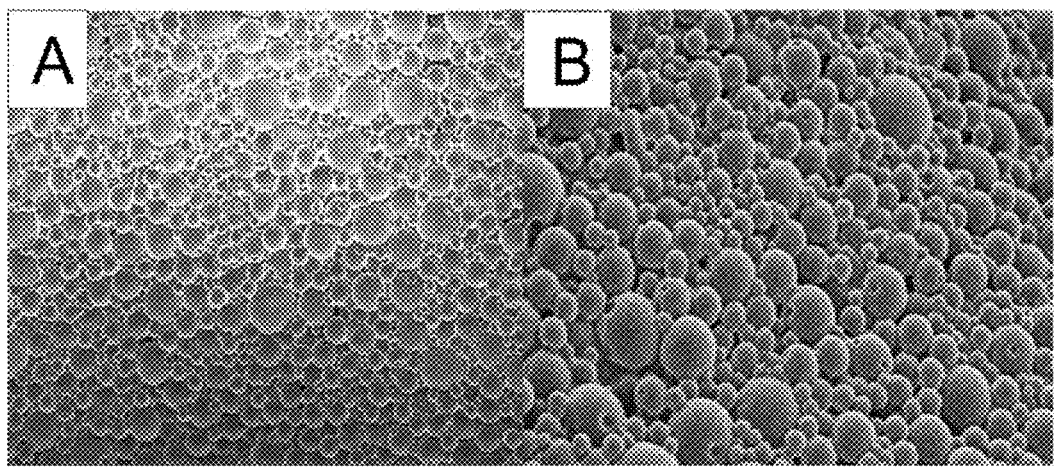

FIG. 7 contains panels showing scanning electron microscopy (SEM) images of exemplary formulations in which (a) MMF to PLA=1:7 (5000× magnification); and (b) MMF to PLA to medium molecular weight chitosan=1:7:7 (10000× magnification).

Figure 8:
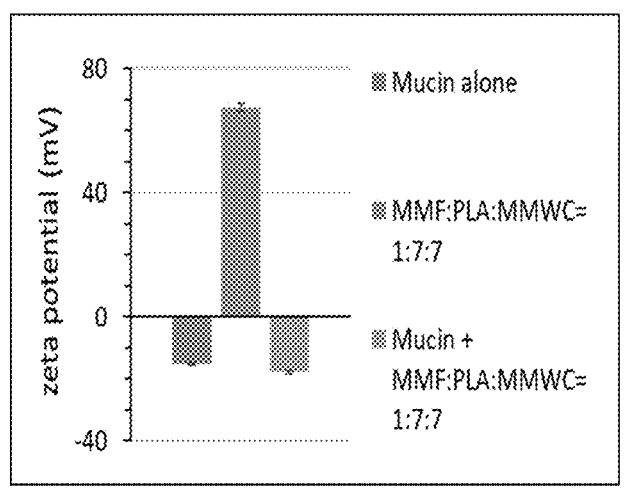

FIG. 8 shows mucin binding of exemplary CS-PNP (MMF to PLA to medium molecular weight chitosan=1:7:7) (n=3, mean±SD). Legend entries represent bars from left to right.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

The present application refers to a number of chemical terms and abbreviations used by those skilled in the art. Nevertheless, definitions of selected terms are provided for clarity and consistency.

As used herein, the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process/method steps. As used herein, the word "consisting" and its derivatives, are intended to be close ended terms that specify the presence of stated features, elements, components, groups, integers, and/or steps, and also exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a nanoparticle" should be understood to present certain aspects with a nanoparticle or two or more nanoparticles. In embodiments comprising an "additional" or "second" component, such as an additional or second nanoparticle, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "subject" as used herein includes all members of the animal kingdom including mammals, and suitably refers to livestock (such as but not limited to bovines) and humans.

The term "pharmaceutical formulation" as used herein refers to a formulation for pharmaceutical use.

The term "for pharmaceutical use" means compatible with the treatment of subjects.

The term "nanoparticle", as used herein, is meant to refer to particles, the average dimensions or diameters of which are less than 300 nm.

The term a "therapeutically effective amount" of a compound of the present disclosure is a quantity sufficient to, when administered to the subject, effect beneficial or desired results, including clinical results, and, as such, a "therapeutically effective amount" or synonym thereto depends upon the context in which it is being applied.

A "therapeutically effective amount" is intended to mean that amount of a compound that is sufficient to treat, prevent or inhibit such diseases or conditions. The amount of a given compound of the present disclosure that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art.

The term "treatment" as used herein, is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The "disease, disorder or condition" as used herein refers to a disease, disorder or condition that benefits from oral administration of mycophenolate mofetil.

The term "formulation of the application" as used herein refers to any formulation comprising polymeric nanoparticles coated with a mucoadhesive polymer, wherein the nanoparticles comprise MMF encapsulated in poly(lactic) acid (PLA) according to the present application.

The term "surfactant" as used herein refers to an amphiphilic compound or mixture of amphiphilic compounds that lowers the surface tension (or interfacial tension) between two liquids or between a liquid and a solid.

The term "% w/w" means a percentage expressed in terms of weight of a component over the total weight of a formulation multiplied by 100.

The term "% w/v" means a percentage expressed in terms of weight of a component over the total volume of a formulation multiplied by 100.

The term "encapsulated" as used herein means that one material is within or entrapped inside and/or throughout a matrix material (typically a polymer). The encapsulation may be by any mechanical, chemical, or other force or bond.

The term "coated" as used herein refers to attachment of a material on the outer surface of another material. The attachment may be partial or whole coverage of the surface of the other material and may be by any mechanical, chemical, or other force or bond.

The term "mucoadhesive polymer" as used herein refers to a material that adheres to or is attracted to a mucosal tissue surface in-vivo and/or in-vitro.

The term "and/or" as used herein refers to and encompasses any and all possible combinations of one or more of the associated listed items.

The term "modified release" as used herein refers to a release of a substance which is not immediate and includes controlled release, extended release, sustained release and delayed release.

The term "sustained release" refers to a release of a substance that occurs over an extended period of time compared to an immediate release form.

The term "mycophenolate mofetil" as used herein refers to a compound having the chemical formula:

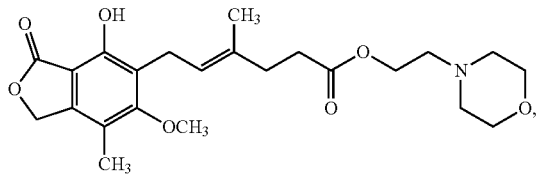 [SMILES: COc1c(C)c2c(c(O)c1C/C=C(\C)CCC(=O)OCCN1CCOCC1)C(=O)OC2]

and includes crystal forms and amorphous forms, for example, but not limited to, polymorphs, solvates, hydrates, and co-crystals.

The term "poly(lactic) acid" as used herein refers to a polymer having the chemical formula:

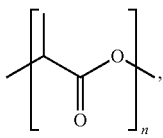

wherein n is a number representing the number of repeating monomers in the polymer.

The term "chitosan" as used herein refers to a polymer having the chemical formula:

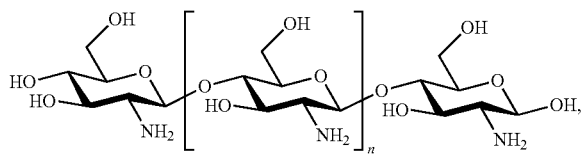

wherein n is a number representing the number of repeating monomers in the polymer.

The term "low molecular weight chitosan" as used herein refers to chitosan having a molecular weight of about 50 kDa to about 190 kDa based on viscosity.

The term "medium molecular weight chitosan" as used herein refers to chitosan having a molecular weight of about 190 kDa to about 310 kDa based on viscosity.

The term "high molecular weight chitosan" as used herein refers to chitosan having a molecular weight of about 310 kDa to greater than about 375 kDa based on viscosity.

A molecular weight (MW) based on viscosity or "viscosity MW" is a well-known method for reporting the MW of polymers. Methods for measuring viscosity MW are known in the art, for example as reported in Kasaai, M. R., Arul, J. and Charlet, G. (2000), Intrinsic viscosity—molecular weight relationship for chitosan. J. Polym. Sci. B Polym. Phys., 38: 2591-2598. The MWs reported herein are those provided by the commercial provider.

The term "medium molecular weight PLA" as used herein refers to PLA having a molecular weight of about 18 kDa to about 24 kDa.

The term "polyvinyl alcohol" as used herein refers to a polymer having the chemical formula:

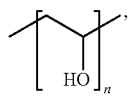

wherein n is a number representing the number of repeating monomers in the polymer.

II. Formulations of the Application

The present application includes a modified release formulation for oral delivery of mycophenolate mofetil (MMF) comprising polymeric nanoparticles coated with a mucoadhesive polymer, wherein the nanoparticles comprise MMF encapsulated in poly(lactic) acid (PLA).

In some embodiments, the mucoadhesive polymer is chitosan. In some embodiments, the chitosan is selected from low molecular weight chitosan, medium molecular weight chitosan and high molecular weight chitosan. In some embodiments, the chitosan is medium molecular weight chitosan. In some embodiments, the chitosan is greater than 75% deacetylated chitosan. In some embodiments, the chitosan is about 75% to about 85% deacetylated.

In some embodiments, the PLA is has a MW of about 10 kDa to about 50 kDa, about 15 kDa to about 30 kDa, or about 18 kDa to about 24 kDa. In some embodiments, the PLA is acid ended polylactic acid.

In some embodiments, the MMF is present in the modified release formulation in an amount effective to treat a specific disease, disorder or condition that benefits from treatment with MMF. In some embodiments, the MMF is present in the formulation in an amount of about 1 mg to about 50 mg, about 2 mg to about 30 mg, about 3 mg to about 20 mg, about 4 mg to about 15 mg, about 5 mg to about 10 mg, or about 7 mg.

In some embodiments, the chitosan is present in the modified release formulation in an amount of about 10 mg to about 74 mg, about 20 mg to about 50 mg or about 21 mg to about 49 mg.

In some embodiments, the PLA is present in the modified release formulation in an amount of about 10 mg to about 75 mg, about 20 mg to about 50 mg or about 21 mg to about 49 mg.

In some embodiments, for example, the modified release formulation comprises about 1 part by weight MMF, about 3 parts to about 7 parts by weight PLA, and about 3 parts to about 7 parts by weight chitosan. In some embodiments, for example, the modified release formulation comprises about 1 part by weight MMF, about 7 parts by weight PLA, and about 7 parts by weight chitosan.

In some embodiments, for example, less than about 60% of MMF is released from a modified release formulation of the application within about 4 hours in simulated gastric fluid at 37° C.

In some embodiments, for example, less than about 80% of MMF is released from a modified release formulation of the application within about 12 hours in simulated gastric fluid at 37° C.

In some embodiments, for example, release of MMF from a modified release formulation of the application is sustained for a period of about 24 hours in simulated gastric fluid at 37° C.

In some embodiments, the polymeric nanoparticles further comprise a surfactant. In some embodiments, the surfactant is polyvinyl alcohol (PVA) or vitamin E D-α-tocopherol polyethylene glycol succinate (vit-E-TPGS). In some embodiments, the surfactant is PVA. In some embodiments, the PVA has a MW of about 5 kDa to about 20 kDa, about 8 kDa to about 15 kDa, or about 9 kDa to about 10 kDa. In some embodiments, the PVA is hydrolyzed PVA. In some embodiments, the PVA is about 70% to about 90% or about 80% hydrolyzed. In some embodiments, the surfactant is present in amounts of about 0.01% to about 0.5% (w/v). In some embodiments, the surfactant is present in trace amounts.

In some embodiments, the formulations of the application further comprise other conventional pharmaceutically acceptable ingredients known to be used in oral delivery formulations. Conventional procedures and ingredients for the selection and preparation of suitable pharmaceutical compositions are described, for example, in Remington's Pharmaceutical Sciences (2000-20th edition) and in The United States Pharmacopeia: The National Formulary (USP 24 NF19) published in 1999.

For example, for oral administration, a formulation of the application may also include an inert diluent or an assimilable edible carrier, or it may be enclosed in hard or soft shell gelatin capsules, or it may be compressed into tablets, or it may be incorporated directly with the food of the diet.

In some embodiments, the formulations are lyophilized and further comprise one or more cryoprotectants. In some embodiments, the cryoprotectants are selected from one or more of trehalose, sucrose and mannitol.

III. Methods and Uses

The formulations of the application may, for example, be useful for the treatment of various diseases, disorders or conditions that benefit from treatment with MMF.

Therefore, the present application also includes a method for treating diseases, disorders or conditions that benefit from treatment with MMF, the method comprising administering a formulation of the present application to a subject in need thereof. The present application further includes a use of a formulation of the present application for treating diseases, disorders or conditions that benefit from treatment with MMF, a use of a formulation of the present application for preparation of a medicament for treating diseases, disorders or conditions that benefit from treatment with MMF, as well as a formulation of the present application for use to treat diseases, disorders or conditions that benefit from treatment with MMF.

In some embodiments, the diseases, disorders or conditions that benefit from treatment with MMF are selected from retroperitoneal fibrosis, lupus nephritis, Behcet's disease, psoriasis, rheumatoid arthritis, inflammatory bowel disease and organ rejection.

In some embodiments, the disease, disorders or condition that benefits from treatment with MMF is organ rejection. Accordingly, the present application also includes a method for treating organ rejection, the method comprising administering an effective amount of a composition of the present application to a subject in need thereof. The present application further includes a use of a formulation of the present application for treating organ rejection, a use of a formulation of the present application for preparation of a medicament for treating organ rejection as well as a formulation of the present application for use to treat organ rejection.

In some embodiments, the organ rejection is as a result of organ transplantation.

In some embodiments, the subject is a mammal. In some embodiments, the subject is human.

Treatment methods comprise administering to a subject a formulation of the application that comprises a therapeutically effective amount of MMF and optionally consist of a single administration, or alternatively comprise a series of administrations. For example, in some embodiments, the formulations of the application may be administered at least once a week. In some embodiments, the formulations may be administered to the subject from about one time per three weeks, or about one time per week to about once daily for a given treatment. In another embodiment, the formulations are administered 2, 3, 4, 5 or 6 times daily. The length of the treatment period depends on a variety of factors, such as the severity of the disease, disorder or condition, the age of the subject, the concentration and/or the activity of the formulations of the application, and/or a combination thereof. It will also be appreciated that the effective dosage of the formulations used for the treatment may increase or decrease over the course of a particular treatment regime. Changes in dosage may result and become apparent by standard diagnostic assays known in the art. In some instances, chronic administration may be required. For example, the formulations are administered to the subject in an amount and for duration sufficient to treat the patient IV. Methods of Preparing The present application also includes a method of preparing the modified release formulations of the application. Therefore the application includes a method or preparing a modified release formulation of mycophenolate mofetil for oral delivery, the method comprising:

a) adding a first solution comprising mycophenolate mofetil and PLA in an organic solvent to an aqueous solution comprising a surfactant under conditions to form a nanoparticle solution; and b) adding the nanoparticle solution to a second solution comprising a mucoadhesive polymer and the surfactant, in an aqueous solvent and stirring to form nanoparticles coated with the mucoadhesive polymer.

In some embodiments, the organic solvent is chloroform or ethyl acetate. In some embodiments, the organic solvent is chloroform.

In some embodiments, the concentration of the PLA in the organic solvent is about 1.5 mg/mL to about 12.5 mg/mL, or about 3 mg/mL to about 8.5 mg/mL.

In some embodiments, the concentration of MMF in the organic solvent is about 0.15 mg/mL to about 8.5 mg/mL. about 0.3 mg/mL to about 5 mg/mL, about 0.5 mg/mL to about 3.5 mg/mL, about 0.7 mg/mL to about 2.5 mg/mL, about 0.8 mg/mL to about 1.7 mg/mL or about 1.2 mg/mL.

In some embodiments, the PLA and MMF are separately dissolved in the organic solvent and the two solutions are combined. In some embodiments, the PLA is dissolved in the organic solvent by vortexing or sonication.

In some embodiments, the concentration of the mucoadhesive polymer in the surfactant solution is about 4 mg/mL to about 10 mg/mL.

In some embodiments, the conditions to form a nanoparticle solution comprise adding the first solution to the aqueous solution at a rate of about 10 mL/min to about 30 ml/min, about 15 mL/min to about 25 ml/min or about 20 ml/min followed by vortexing and sonicating. In some embodiments, the vortexing is for about 5 sec to about 30 sec, about 10 sec to about 20 sec or about 15 sec. In some embodiments, the sonicating is for about 1 min to about 10 min, about 3 min to about 8 min or about 5 min. In some embodiments, the sonicating is done in about 20 sec bursts with about 10 sec rest in between each burst. In some embodiments, the sonicating is performed at about 40% amplitude using an about ⅛ inch tip size probe. In some embodiments, the tip of the probe is moved up and down through the nanoparticle solution.

In some embodiments, the mucoadhesive polymer is dissolved in a dilute acid solution, such as dilute acetic acid prior to being combined with the surfactant. In some embodiments, the concentration of the acid solution is about 1% (v/v) to about 5% (v/v) or about 2% (v/v).

In some embodiments the surfactant is used as an about 0.1% (w/v) to about 1.0% (w/v) or about 0.5% (w/v) aqueous solution.

In some embodiments, the nanoparticle solution is added to the second solution at a rate of about 10 mL/min to about 30 ml/min, about 15 mL/min to about 25 ml/min or about 20 ml/min followed by stirring for about 1 hour to about 10 hours, about 3 hours to about 8 hours or about 6 hours.

In some embodiments, the method is performed at or about room temperature, or about 20° C. to about 25° C.

In some embodiments, the coated nanoparticles are collected from the solution. In some embodiments, the nanoparticles are collected by centrifugation. In some embodiments, the nanoparticles are washed with distilled water one or more, for example one to three times.

In some embodiments, the coated nanoparticles are suspended in distilled water and a cryoprotectant is added and the nanoparticles are lyophilized. In some embodiments, the cryoprotectant is sucrose, trehalose, lactose, mannitol or polyethylene glycol, or a mixture thereof. In some embodiments, the cryoprotectant is sucrose. In some embodiments, the cryoprotectant is a 5% (w/v) solution in distilled water.

The following non-limiting examples are illustrative of the present application:

EXAMPLES

Example 1

Chitosan-Coated Polymeric Nanoparticles

Materials and Methods

MMF (99.9% pure) was purchased from Sigma Aldrich (Canada). Resomer RG 752H (acid end polylactic-co-glycolic acid (PLGA) 75:25, MW: 4000-15000), Resomer RG 653H (acid end polylactic-co-glycolic acid (PLGA) 65:35, MW: 24000-38000) and Resomer R 203H (acid end polylactic acid (PLA), MW: 18000-24000) were purchased from Sigma Aldrich (Canada). Low (50-190 kDa and 75-85% deacetylated), medium (75-85% deacetylated) and high (310-375 kDa and >75% deacetylated) molecular weight chitosan were purchased from Sigma Aldrich (Canada). PVA (MW 9000-10000 Da, 80% hydrolyzed) was purchased from Sigma Aldrich (Canada). All the solvents used were of analytical grade.

Preparation of PNPs

PNPs were prepared by modified emulsion based solvent evaporation method (Sharma, N. et al.) using the amount recited in Table 1. Briefly, MMF and low molecular weight (MW) PLGA/high MW PLGA/med MW PLA were dissolved in chloroform and added to 0.5% w/v polyvinyl alcohol (PVA) on a vortex mixer at a constant rate of 20 mL/min with syringe pump (NE-1000, New Era syringe pump, USA). The primary emulsion was then size-reduced by ultra-sonication for 5 min at 40% amplitude using ⅛" probe tip (Branson digital Sonifier™ 250). Then, the emulsion was added a constant rate of 20 mL/min using syringe pump to 5 mL of 0.5% w/v PVA in a beaker and allowed to harden for 3 h by constant stirring at 300 rpm. After hardening, the PNPs were centrifuged and washed three times to remove excess surfactant. The PNP pellet after the third wash was suspended in 4 mL of deionized water. Cryoprotectant, 1 mL of sucrose (5% w/w) was added to each formulation. The final PNP suspension (5 mL) was frozen to −80° C. and lyophilized for 72 h. PNPs after lyophilization were stored at 4° C. until further characterization.

Preparation of Chitosan Coated PNPs

Chitosan coated PNPs (CS-PNPs) were prepared using the amounts recited in Table 2 similar to the above method with slight modifications (Manca, M. L., 2008) as follows. Chitosan (low, medium or high MW) was dissolved in dilute acetic acid (2% v/v) and added to the beaker containing 0.5% w/v PVA and allowed to harden for 6 h.

HPLC Method Development of Mycophenolate Mofetil (MMF)

An HPLC method for the quantification of MMF was developed on a Waters 2695 Separations module equipped with Waters 2996 photodiode array detector. MMF was separated on Luna® C8 column (Phenomenex®, USA) with 5 μm particle size and 30×2 mm dimensions. The mobile phase used was 0.3% triethylamine (TEA), pH 5.3 [pH adjusted with trifluoroacetic acid (TFA)] and acetonitrile at a ratio of 70:30 (v:v) respectively, and the flow rate was 0.4 mL/min. with column temperature set to 45° C. The retention time (RT) was 2.4 min. An external calibration curve was developed by preparing standard solutions in methanol and the range was 2-60 μg/mL. ($r^2$>0.9996). The limit of quantification was 2 μg/mL and the limit of detection was 1 μg/mL and percentage relative standard deviation (RSD) of inter-day precision (0.85%) based on the external standards was within limits (<2%).

Particle Size, Polydispersity and Zeta Potential

The mean particle size (nm), polydispersity index (PDI) and zeta potential (mV) of PNPs and CS-PNPs were determined by dynamic light scattering (Nano ZS, Malvern). Briefly, 300 μg of sample was dispersed in 1 mL deionized water and ultrasonicated (⅛" probe) for 10 s at 10% amplitude before analysis. All the measurements were made in triplicates at 25° C. and reported as mean±SD.

Encapsulation Efficiency

The encapsulation efficiency (EE) was measured by weighing 500 μg of PNP and adding 1 mL of acetone followed by water bath sonication for 1 h. The acetone was evaporated under vacuum, and a triple solvent extraction was performed: In the first extraction step, methanol was added to extract the drug followed by centrifugation at 14000 rpm for 10 min. The supernatant (first extract) was gently separated with the help of pipette and saved for quantification of drug content. This procedure was repeated with the PNP sample twice more to maximize drug extraction yielding second and third extract. Drug content was quantified in all the extractions and the encapsulation efficiency was calculated according to equation-1.

$$EE = \frac{(MMF \text{ in } 1st \text{ extract} + MMF \text{ in } 2nd \text{ extract} + MMF \text{ in } 3rd \text{ extract})}{MMF \text{ added in } PNP \text{ or } CS\text{-}PNP} \times 100 \quad \text{Equation (1)}$$

The encapsulation efficiency of CS-PNPs was estimated in a manner similar to the above method except for the addition of 2% v/v acetic acid (AA), bath sonication for 1 h and evaporation of AA prior to prior to addition of acetone.

In Vitro Drug Release Study

Pre-weighed (6 mg) PNPs or CS-PNPs were suspended in deionized water (2 mL) and subjected to an in vitro release study to understand the release behavior of MMF from the nanoparticles. Using a dialysis membrane (MW cut off 12000-14000), the dialysis bag was suspended in 900 mL simulated gastric fluid, USP (SGF) for two hours followed by 900 mL simulated intestinal fluid, USP (SIF) for up to 24 h. The media was stirred in a 1 L beaker at 100 rpm and maintained at 37±2° C. At predetermined time intervals; 0, 1, 2, 4, 6, 12 and 24 h, 100 μL of sample was collected from the dialysis bag and the drug content was determined by procedure described above.

Scanning Electron Microscopy (SEM)

The surface morphology of PNPs and CS-PNPs was studied using a scanning electron microscope (Hitachi SU8000). Prior to the analysis, the samples were fixed on a brass stub using double-sided tape and the samples were coated with chromium (to render them electrically conductive). The images were then captured using SEM set at an excitation voltage of (3.0 kV). The magnification selected (400-10K) was sufficient to appreciate in detail the general morphology of the samples under study.

Mucin Binding Studies

The mucoadhesiveness of CS-PNPs was assessed by measuring zeta potential changes upon addition of mucin protein solution. Briefly, the optimal CS-PNP formulation (300 μg) was added to mucin (5 mg/mL) and incubated for 1 h followed by analyzing zeta potential. The zeta potential of mucin and of the optimal CS-PNPs in water were also estimated, serving as controls.

Statistical Analysis

The data obtained was subjected to one-way analysis of variance (ANOVA), and the significance of differences between any two formulations was calculated by Tukey's post-hoc test with SPSS software (IBM, New York, USA). The level of significance chosen was $p<0.05$.

Results and Discussion

Preparation of Nanoparticles

There are several methods available for preparing PNPs or CS-PNPS such as variations on emulsion-based solvent evaporation methods, ionotropic gelation and complex coacervation technique (Mohammed, M. et al., 2017). The method utilized here for the preparation of PNPs and CS-PNPs was an emulsion-based solvent evaporation method with slight modifications. Although the aim was to develop CS-coated PNPs, initially uncoated PNPs were prepared first with low MW PLGA/high MW PLGA/medium MW PLA using the amounts as recited in Table 1 to derive an optimal formulation maximizing encapsulation efficiency. Later, CS-PNPs were prepared by adding different types of chitosan to the optimal PNP formulation. In the course of the initial experiments it was determined that acid-end capped PLGA or PLA polymers generated PNPs with better entrapment compared to the ester terminated polymers for the drug. While not wishing to be limited by theory, this may be related to their greater water solubility and subsequent NP formation characteristics. PLGA/PLA with ester termination take 4-6 weeks to degrade compared to acid end when kept in a dissolution medium (Félix Lanao, R. P. et al. 2013).

Particle Size, Polydispersity and Zeta Potential

One parameter that is relevant for nanoparticle performance is particle size (Table 3) and size distribution. The lesser the particle size, the more surface area is available for dissolution. Size distribution is a consideration because monodisperse particles permit more predictable control over drug release. The polydispersity index (PDI) is the indication of size distribution and all the values in Table 3 are below 0.4, which indicates unimodal size distribution. As, shown in Table 3, the zeta potential of all the formulations was negative owing to the charge of PLGA/PLA. The aim was to prepare NPs with a positive surface charge, because NPs with a positive charge can bind to negatively charged mucous (mucoadhesion), thereby potentially increasing retention in the gastrointestinal tract and prolonging drug release. A positive surface charge may be achieved by coating the PNPs with chitosan. As the ratio of drug to polymer increases, particle size should also increase, and this trend is evident from FIG. 1.

The particle size, PDI and zeta potential of CS-PNPs are shown in Table 4 and FIG. 2. There is a change in zeta potential from negative to positive. However, this happens only with the formulations made with medium MW PLA and medium and high molecular weight chitosan. However, the particle size of some of the formulations was found to be very high which, while not wishing to be limited by theory could be due to the stress during lyophilization (Fonte, P., et al., 2016). The particle size of CS-PNPs was estimated before lyophilization and it was found to be below 300 nm as shown in Table 5. Generally, cryoprotectants are added during lyophilization to reduce freezing or drying stress thereby enhancing the stability of PNPs. Trehalose, sucrose and mannitol are most commonly used cryoprotectants which yield different sized PNPs and affect their stability (Almalik, A. et al., 2017).

Encapsulation Efficiency

The encapsulation efficiency of PNPs was between 61-104% as represented in FIG. 3. These results suggest that the encapsulation efficiency of MMF is dependent on the amount of polymer. As the polymer used in preparing PNPs has an acid end, the encapsulation efficiency of all the PNPs was found to be relatively high. However, there is no significant difference between some of the formulations when compared to each other such as; MMF: low MW PLGA=1:5 and MMF: low MW PLGA=1:7, MMF:medium MW PLA=1:5 and MMF:medium MW PLA=1:7.

The encapsulation efficiency of CS-PNPs as a function of polymer type and drug: polymer ratio is represented in FIG. 4. The encapsulation efficiency of MMF:PLA:LMWC=1:3:3 is less than MMF:PLA=1:3 which, while not wishing to be limited by theory could be due to the drug loss during the chitosan coating. However, the addition of different types of chitosan did not reduce the encapsulation efficiency significantly at least at the highest polymer ratios (1:7:7).

In Vitro Drug Release

A significant burst effect (>50% of drug) was seen in PNPs made with low MW PLGA and high MW PLGA within 2 h in SGF (FIGS. 5a and 5b). With the PNPs made with MMF and low MW PLGA; at 1:3 ratio almost all the drug was released in 6 h, while with 1:5 and 1:7 drug:polymer ratio, approximately 65% of the drug was released within 2 h in SGF and rest of the drug was more slowly released in SIF until 24 h. There is no significant difference between the release profile of PNPs made with low MW PLGA, ratio of 1:5 and 1:7 at 2, 4, 6, 12 and 24 h. However, the drug release is less when the drug to polymer ratio has been increased from 1:3 to 1:5. The slight delay in the drug release with high MW PLGA compared to low MW PLGA may be because of the molecular weight, chain length and lactic acid content in the polymer (Mittal, G, et al, 2007). High molecular weight and hydrophobicity of lactic acid delays the polymer degradation which further delays the drug release. The ratio of drug to polymer plays a role in drug release as evident in FIG. 5b. As PLA is the most lipophilic of all the polymers used, drug release is further delayed and with 1:7 drug to polymer ratio, a minimal burst release (20%) and a desirable sustained release profile until 24 h can be seen. Drug release from PLGA and PLA nanoparticles is generally governed by diffusion-degradation process. More specifically, in the early hours of drug release in media, a diffusion process dominates, which is then followed by degradation of the polymer matrix in the later hours (Mogi, T, et al. 2000). Overall, the MMF PNPs made here with PLA show sustained release up to 24 h with minimal burst release, therefore, they were chosen as the most optimal formulation and chitosan coating was performed subsequently for these formulations.

As mentioned above, the reason behind coating the PNPs with chitosan is to provide a positive charge on the PNPs and also to minimize the burst release within 2 h in SGF as shown in FIG. 6. With MMF:PLA:LMWC=1:3:3, about 45% of drug released within 2 h which may suggest that a lesser degree of chitosan coating was achieved, which was supported by zeta potential data (−22.1 mV). The CS-PNPs made with medium MW chitosan have shown minimal burst release (<25%) within 2 h with the ratio 1:5:5 and 1:7:7. Although there is no significant difference at 1, 2 and 4 h between them, MMF:PLA:MMWC=1:7:7 has shown sustained released up to 24 h. CS-PNPs made with PLA and HMWC have shown significant burst release due to the high molecular weight of chitosan. The burst release of MMF could be due to swelling of chitosan. Although there is burst release, the drug release after 2 h is well controlled with MMF:PLA:HMWC=1:5:5 and 1:7:7. Some studies in the literature report thick gel formation around the nanoparticles after slow dissolution of high MW chitosan (Yang, H.-C., et al., 2009). With the above results, MMF:PLA:MMWC=1: 7:7 was chosen as the optimal formulation and subject to further characterization such as mucoadhesiveness and surface morphology.

Scanning Electron Microscopy.

SEM analysis revealed that the PNPs and CS-PNPs are spherical and correspond to the unimodal size distribution seen by dynamic light scattering experiments. The nanoparticles exhibit smooth surface and minimal pores as seen in FIG. 7.

Mucin Binding Studies.

Mucin alone shows a negative zeta potential and MMF:PLA:MMWC=1:7:7 alone shows positive zeta potential. But, when MMF:PLA:MMWC=1:7:7 is mixed with mucin, a complex is formed due to the electrostatic attraction between chitosan and mucin resulting in charge reversal of MMF:PLA:MMWC=1:7:7 as indicated in FIG. 8.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERENCED IN THE APPLICATION

Ahmad, Z.; Pandey, R.; Sharma, S.; Khuller, G. K. Alginate nanoparticles as antituberculosis drug carriers: formulation development, pharmacokinetics and therapeutic potential. Indian J. Chest Dis. Allied Sci. 2006, 48, 171-6.

Almalik, A.; Alradwan, I.; Kalam, M. A.; Alshamsan, A. Effect of cryoprotection on article size stability and preservation of chitosan nanoparticles with and without hyaluronate or alginate coating. Saudi Pharm. J. 2017, 25, 861-867, doi: 10.1016/j.jsps.2016.12.008.

Budhian, A.; Siegel, S. J.; Winey, K. I. Production of haloperidol-loaded PLGA nanoparticles for extended controlled drug release of haloperidol. J. Microencapsul. 2005, 22, 773-785, doi:10.1080/02652040500273753.

Chakravarthi, S. S.; Robinson, D. H. Enhanced cellular association of paclitaxel delivered in chitosan-PLGA particles. Int. J. Pharm. 2011, 409, 111-120, doi:10. 1016/j.ijpharm.2011.02.034.

Chen, H. et al. Chitosan Surface-Modified PLGA Nanoparticles: Preparation, Characterization, and Evaluation of their In Vitro Drug-Release Behaviors and Cytotoxicities, *Current Nanoscience,* 2014, 10(2):255-262.

Cheng, Q.; Feng, J.; Chen, J.; Zhu, X.; Li, F. Brain transport of neurotoxin-I with PLA nanoparticles through intranasal administration in rats: a microdialysis study. Biopharm. Drug Dispos. 2008, 29, 431-439, doi:10.1002/bdd.621.

Cho, D.; Reineke, J.; Mathiowitz, E.; Laulicht, B. Nanoparticle compositions and methods for improved oral delivery of active agents. U.S. Pat. No. 8,673,359 (filed 8 Jul. 2011).

Chronopoulu, L. et al. Chitosan-coated PLGA nanoparticles: A sustained drug release strategy for cell cultures, Colloids and Surfaces B. Biointerfaces, 2013, 103:310-317.

Damgé, C.; Maincent, P.; Ubrich, N. Oral delivery of insulin associated to polymeric nanoparticles in diabetic rats. J. Control. Release 2007, 117, 163-170, doi: 10.1016/j.jconrel.2006.10.023.

Dev A., et al. Preparation of poly(lactic acid)/chitosan nanoparticles for anti-HIV drug delivery applications, *Carbohydrate Polymers,* 2010, 80: 833-838.

Dew, M. A., DiMartini, A. F., De Vito Dabbs, A., Myaskovsky, L., Steel, J., Unruh, M., Switzer, G. E., Zomak, R., Kormos, R. L., Greenhouse, J. B. Rates and risk factors for nonadherence to the medical regimen after adult solid organ transplantation. *Transplantation.* 2007 Apr. 15; 83(7):858-73. PubMed PMID: 17460556.

Félix Lanao, R. P.; Jonker, A. M.; Wolke, J. G. C.; Jansen, J. A.; Van Hest, J. C. M.; Leeuwenburgh, S. C. G. Physicochemical Properties and Applications of Poly(lactic-co-glycolic acid) for Use in Bone Regeneration. Tissue Eng. Part B 2013, 19, 380-390, doi:10.1089/ten-.teb.2012.0443.

Fonte, P.; Reis, S.; Sarmento, B. Facts and evidences on the lyophilization of polymeric nanoparticles for drug delivery. J. Control. Release 2016, 225, 75-86, doi:10.1016/j.jconrel.2016.01.034.

Fujiyama, N.; Miura, M.; Kato, S.; Sone, T.; Isobe, M.; Satoh, S. Involvement of Carboxylesterase 1 and 2 in the Hydrolysis of Mycophenolate Mofetil. Drug Metab. Dispos. 2010, 38, 2210-17., doi:10.1124/dmd.110.034249.

Gomezgaete, C.; Tsapis, N.; Besnard, M.; Bochot, A.; Fattal, E. Encapsulation of dexamethasone into biodegradable polymeric nanoparticles. Int. J. Pharm. 2007, 331, 153-159, doi:10.1016/j.ijpharm.2006.11.028.

Guo, M. et al. Mechanisms of chitosan-coated poly(lactic-co-glycolic acid) nanoparticles for improving oral absorption of 7-ethyl-10-hydroxycamptothecin, *Nanotechnology,* 2013, 24:245101.

He, X.; Smeets, R. L.; Koenen, H. J. P. M.; Vink, P. M.; Wagenaars, J.; Boots, A. M. H.; Joosten, I. Mycophenolic Acid-Mediated Suppression of Human CD4+ T Cells: More Than Mere Guanine Nucleotide Deprivation. Am. J. Transplant. 2011, 11, 439-449, doi:10.1111/j.1600-6143.2010.03413.x.

Kumari, A.; Yadav, S. K.; Yadav, S. C. Biodegradable polymeric nanoparticles based drug delivery systems. Colloids Surfaces B Biointerfaces 2010, 75, 1-18, doi: 10.1016/j.colsurfb.2009.09.001.

Manca, M. L.; Loy, G.; Zaru, M.; Fadda, A. M.; Antimisiaris, S. G. Release of rifampicin from chitosan, PLGA and chitosan-coated PLGA microparticles. Colloids Surfaces B Biointerfaces 2008, 67, 166-170, doi:10.1016/j.colsurfb.2008.08.010.

Mittal, G.; Sahana, D. K.; Bhardwaj, V.; Ravi Kumar, M. N. V Estradiol loaded PLGA nanoparticles for oral administration: Effect of polymer molecular weight and copolymer composition on release behavior in vitro and in vivo. J. Control. Release 2007, 119, 77-85, doi:10.1016/j.jconrel.2007.01.016.

Mogi, T.; Ohtake, N.; Yoshida, M.; Chimura, R.; Kamaga, Y.; Ando, S.; Tsukamoto, T.; Nakajima, T.; Uenodan, H.; Otsuka, M.; Matsuda, Y.; Ohshima, H.; Makino, K. Sustained release of 17β-estradiol from poly (lactide-co-glycolide) microspheres in vitro and in vivo. Colloids Surfaces B Biointerfaces 2000, 17, 153-165, doi:10.1016/S0927-7765(99)00105-8.

Mohammed, M.; Syeda, J.; Wasan, K.; Wasan, E. An Overview of Chitosan Nanoparticles and Its Application in Non-Parenteral Drug Delivery. Pharmaceutics 2017, 9, 53, doi:10.3390/pharmaceutics9040053.

Mu, L.; Feng, S. S. A novel controlled release formulation for the anticancer drug paclitaxel (Taxol): PLGA nanoparticles containing vitamin E TPGS. J. Control. Release 2003, 86, 33-48.

Nafee, N. et al. Chitosan-coated PLGA nanoparticles for DNA/RNA delivery: Effect of the formulation parameters on complexation and transfection of antisense oligonucleotides, Nanomedicine: nanotechnology, biology and medicine, 2007 3(3):173-183.

Nagarwal, R. C. et al. Chitosan coated PLA nanoparticles for ophthalmic delivery: characterization, in-vitro and in-vivo study in rabbit eye, J Biomed Nanotechnology, 2010, 6(6) 648-57.

Palacio, J.; Agudelo, N. A.; Lopez, B. L. PEGylation of PLA nanoparticles to improve mucus-penetration and colloidal stability for oral delivery systems. Curr. Opin. Chem. Eng. 2016, 11, 14-19, doi:10.1016/j.coche.2015.11.006.

Pandit, J. et al. Chitosan-coated PLGA nanoparticles of bevacizumab as novel drug delivery to target retina: optimization, characterization, and in vitro toxicity evaluation, Artif Cells Nanomed Biotech, 2017, 45(7):1397-1407.

Parfitt, J. R.; Jayakumar, S.; Driman, D. K. Mycophenolate mofetil-related gastrointestinal mucosal injury: variable injury patterns, including graft-versus-host disease-like changes. Am. J. Surg. Pathol. 2008, 32, 1367-72.

Park, J S. A sustained releasing agent of an immunosuppressant comprising mycophenolate mofetil. Patent No. KR1020110091252A (filed 5 Feb. 2010).

Ponticelli, C., Scolari, M. P. Calcineurin inhibitors in renal transplantation still needed but in reduced doses: a review. Transplant Proc. 2010 July-August; 42(6):2205-8. doi: 10.1016/j.transproceed.2010.05.036. Review. PubMed PMID: 20692445.

Sharma, N.; Madan, P.; Lin, S. Effect of process and formulation variables on the preparation of parenteral paclitaxel-loaded biodegradable polymeric nanoparticles: A co-surfactant study. Asian J. Pharm. Sci. 2016, 11, 404-416, doi:10.1016/j.ajps.2015.09.004.

Singh, P. K. et al. Macrophage-targeted chitosan anchored PLGA nanoparticles bearing doxorubicin and amphotericin B against visceral leishmaniasis, RSC Advances, 2016, 6:71707-71718.

Vila, A.; Sanchez, A.; Tobio, M.; Calvo, P.; Alonso, M. J. Design of Biodegradable Partilces for Protein Delivery. J. Control. Release 2002, 78, 15-24.

Wang Y. et al. Chitosan-modified PLGA nanoparticles with versatile surface for improved drug delivery. AAPS PharmSciTech 2013, 14(2):585-592.

Yang, H.-C.; Hon, M.-H. The effect of the molecular weight of chitosan nanoparticles and its application on drug delivery. Microchem. J. 2009, 92, 87-91, doi: 10.1016/j.microc.2009.02.001.

Yuan, X. B. et al. Preparation of rapamycin-loaded chitosan/PLA nanoparticles for immunosuppression in corneal transplantation, Int. J. Pharm, 2008, 12:241-248.

Yuancai, D. Chitosan-coated PLGA Nanoparticles for Oral Administration of Paclitaxel, Chapter 5; downloaded from Scholarbank.nus.edu.

TABLE 1

Comparative and exemplary embodiments of PNP formulations made with MMF and (a) low MW PLGA; (b) high MW PLGA; and (c) med MW PLA

| Formulation* | MMF (mg) | Low MW PLGA (mg) | PVA (% w/v) |
|---|---|---|---|
| MMF:Low MW PLGA = 1:3 | 7 | 21 | 0.5 |
| MMF:Low MW PLGA = 1:5 | 7 | 35 | 0.5 |
| MMF:Low MW PLGA = 1:7 | 7 | 49 | 0.5 |
| | | High MW PLGA (mg) | |
| MMF:High MW PLGA = 1:3 | 7 | 21 | 0.5 |
| MMF:High MW PLGA = 1:5 | 7 | 35 | 0.5 |
| MMF:High MW PLGA = 1:7 | 7 | 49 | 0.5 |
| | | Med MW PLGA (mg) | |
| MMF:Med MW PLA = 1:3 | 7 | 21 | 0.5 |
| MMF:Med MW PLA = 1:5 | 7 | 35 | 0.5 |
| MMF:Med MW PLA = 1:7 | 7 | 49 | 0.5 |

TABLE 2

Comparative and exemplary embodiments of CS-PNP formulations made with medium MW PLA and (a) low MW chitosan; (b) high MW chitosan; and (c) med MW chitosan

| Formulation* | MMF (mg) | Med MW PLA (mg) | Low MW Chitosan (mg) | PVA (% w/v) |
|---|---|---|---|---|
| MMF:Med MW PLA:LMWC = 1:3:3 | 7 | 21 | 21 | 0.5 |
| MMF:Med MW PLA:LMWC = 1:5:5 | 7 | 35 | 35 | 0.5 |
| MMF:Med MW PLA:LMWC = 1:7:7 | 7 | 49 | 49 | 0.5 |
| | | | Medium MW Chitosan (mg) | |
| MMF:Med MW PLA:MMWC = 1:3:3 | 7 | 21 | 21 | 0.5 |

TABLE 2-continued

Comparative and exemplary embodiments of CS-PNP formulations made with medium MW PLA and (a) low MW chitosan; (b) high MW chitosan; and (c) med MW chitosan

| Formulation* | MMF (mg) | Med MW PLA (mg) | MMWC (mg) | PVA (% w/v) |
|---|---|---|---|---|
| MMF:Med MW PLA:MMWC = 1:5:5 | 7 | 35 | 35 | 0.5 |
| MMF:Med MW PLA:MMWC = 1:7:7 | 7 | 49 | 49 | 0.5 |

| Formulation* | MMF (mg) | Med MW PLA (mg) | High MW Chitosan (mg) | PVA (% w/v) |
|---|---|---|---|---|
| MMF:Med MW PLA:HMWC = 1:3:3 | 7 | 21 | 21 | 0.5 |
| MMF:Med MW PLA:HMWC = 1:5:5 | 7 | 35 | 35 | 0.5 |
| MMF:Med MW PLA:HMWC = 1:7:7 | 7 | 49 | 49 | 0.5 |

TABLE 3

Particle size, polydispersity index, and zeta potential of PNPs made with MMF and (a) low MW PLGA (comparative); (b) high MW PLGA (comparative); and (c) med MW PLA (exemplary)

| Formulation | Particle size (nm) Mean | SD | PDI Mean | SD | Zeta potential (mV) Mean | SD |
|---|---|---|---|---|---|---|
| MMF:Low MW PLGA = 1:3 | 316.7 | 33.3 | 0.278 | 0.02 | −42.5 | 1.33 |
| MMF:Low MW PLGA = 1:5 | 405.7 | 25.6 | 0.292 | 0.05 | −45.2 | 1.75 |
| MMF:Low MW PLGA = 1:7 | 752 | 28.2 | 0.325 | 0.03 | −49.5 | 0.719 |
| MMF:High MW PLGA = 1:3 | 230 | 15.4 | 0.38 | 0.048 | −41 | 1.3 |
| MMF:High MW PLGA = 1:5 | 319.6 | 27.3 | 0.259 | 0.169 | −41.3 | 1.86 |
| MMF:High MW PLGA = 1:7 | 841.5 | 26.5 | 0.067 | 0.004 | −43.5 | 0.465 |
| MMF:Med MW PLA = 1:3 | 369.3 | 19.25 | 0.161 | 0.13 | −30.2 | 0.883 |
| MMF:Med MW PLA = 1:5 | 580 | 24.7 | 0.343 | 0.042 | −30.5 | 1.97 |
| MMF:Med MW PLA = 1:7 | 931.5 | 12.22 | 0.312 | 0.049 | −37 | 1.43 |

TABLE 4

Particle size, polydispersity index, and zeta potential of exemplary embodiments of PNPs made with MMF, PLA and (a) low MW chitosan; (b) medium MW chitosan; and (c) high MW chitosan

| Formulation | Particle size (nm) Mean | SD | PDI Mean | SD | Zeta potential (mV) Mean | SD |
|---|---|---|---|---|---|---|
| MMF:PLA:LMWC = 1:3:3 | 221.8 | 35.99 | 0.27 | 0.04 | −22.1 | 1.35 |
| MMF:PLA:LMWC = 1:5:5 | 340.4 | 49.21 | 0.32 | 0.02 | −24.8 | 1.53 |
| MMF:PLA:LMWC = 1:7:7 | 532.6 | 52.7 | 0.37 | 0.03 | −14.9 | 2.48 |
| MMF:PLA:MMWC = 1:3:3 | 281.2 | 53.36 | 0.31 | 0.06 | 24.4 | 1 |
| MMF:PLA:MMWC = 1:5:5 | 995 | 34.7 | 0.23 | 0.04 | 53.8 | 1.31 |
| MMF:PLA:MMWC = 1:7:7 | 1194 | 51.4 | 0.14 | 0.01 | 67.6 | 1.29 |
| MMF:PLA:HMWC = 1:3:3 | 390.5 | 69 | 0.33 | 0.05 | 41.8 | 0.98 |
| MMF:PLA:HMWC = 1:5:5 | 1079 | 63.9 | 0.24 | 0.04 | 50.4 | 2.53 |
| MMF:PLA:HMWC = 1:7:7 | 1336 | 63.88 | 0.20 | 0.02 | 61.2 | 1.42 |

TABLE 5

Particle size comparison of exemplary embodiments of CS-PNPs before and after lyopholization

| Formulation | Particle size (nm) before lyophilization Mean* | SD | Particle size (nm) after lyophilization Mean** | SD |
|---|---|---|---|---|
| MMF:PLA:LMWC = 1:3:3 | 182.7 | 36.5 | 221.8 | 35.99 |
| MMF:PLA:LMWC = 1:5:5 | 284.6 | 54.2 | 340.4 | 49.21 |
| MMF:PLA:LMWC = 1:7:7 | 447.2 | 46.8 | 532.6 | 52.7 |
| MMF:PLA:MMWC = 1:3:3 | 196.8 | 43 | 281.2 | 53.36 |
| MMF:PLA:MMWC = 1:5:5 | 257.8 | 37.2 | 1295 | 34.7 |
| MMF:PLA:MMWC = 1:7:7 | 430.4 | 24.6 | 1194 | 51.4 |
| MMF:PLA:HMWC = 1:3:3 | 160.8 | 66.1 | 390.5 | 69 |
| MMF:PLA:HMWC = 1:5:5 | 319.4 | 79.1 | 1079 | 63.9 |
| MMF:PLA:HMWC = 1:7:7 | 440.2 | 35.1 | 1336 | 63.88 |

The invention claimed is:

1. A modified release formulation for oral delivery of mycophenolate mofetil (MMF) comprising polymeric nanoparticles coated with a mucoadhesive polymer, wherein the nanoparticles comprise MMF encapsulated in poly(lactic) acid (PLA), wherein the PLA as a molecular weight (MW) of about 18 kDa to about 24 kDa and the PLA is acid ended polylactic acid.

2. The modified release formulation of claim 1, wherein the mucoadhesive polymer is chitosan.

3. The modified release formulation of claim 2, wherein the chitosan is medium molecular weight chitosan.

4. The modified release formulation of claim 3, wherein the chitosan is greater than 75% deacetylated chitosan.

5. The modified release formulation of claim 1, wherein the MMF is present in the modified release formulation in an amount effective to treat a specific disease, disorder or condition that benefits from treatment with MMF.

6. The modified release formulation of claim 1, wherein the MMF is present in the formulation in an amount of about 1 mg to about 50 mg, about 2 mg to about 30 mg, about 3 mg to about 20 mg, about 4 mg to about 15 mg, about 5 mg to about 10 mg, or about 7 mg.

7. The modified release formulation of claim 1, wherein the chitosan is present in the modified release formulation in an amount of about 10 mg to about 75 mg, about 20 mg to about 50 mg or about 21 mg to about 49 mg.

8. The modified release formulation of claim 7, further comprising polyvinyl alcohol, wherein the polyvinyl alcohol is present in the modified release formulation in an amount of about 0.1% w/v to about 1.0% w/v, or about 0.5% w/v.

9. The modified release formulation of claim 1, wherein the PLA is present in the modified release formulation in an amount of about 10 mg to about 74 mg, about 20 mg to about 50 mg or about 21 mg to about 49 mg.

10. The modified release formulation of claim 1, wherein the modified release formulation comprises about 1 part by weight MMF, about 3 parts to about 7 parts by weight PLA, and about 3 parts to about 7 parts by weight chitosan or about 1 part by weight MMF, about 7 parts by weight PLA, and about 7 parts by weight chitosan.

11. The modified release formulation of claim 1, wherein, less than about 60% of MMF is released from a modified release formulation of the application within about 4 hours in simulated gastric fluid at 37° C.

12. The modified release formulation of claim 1, wherein less than about 80% of MMF is released from a modified release formulation of the application within about 12 hours in simulated gastric fluid at 37° C.

13. A method for treating diseases, disorders or conditions that benefit from treatment with MMF, the method comprising administering the formulation of claim 1 to a subject in need thereof.

14. The method of claim 13, wherein the diseases, disorders or conditions that benefit from treatment with MMF are selected from retroperitoneal fibrosis, lupus nephritis, Behcet's disease, psoriasis, rheumatoid arthritis, inflammatory bowel disease and organ rejection.

15. The method of claim 14, wherein the disease, disorders or condition that benefits from treatment with MMF is organ rejection.

16. A method of preparing the modified release formulation of mycophenolate mofetil for oral delivery comprising polymeric nanoparticles coated with a mucoadhesive polymer of claim 1, the method comprising:
  a) adding a first solution comprising the mycophenolate mofetil and the PLA in an organic solvent to an aqueous solution comprising a surfactant under conditions to form a nanoparticle solution; and
  b) adding the nanoparticle solution to a second solution comprising the mucoadhesive polymer and the surfactant, in an aqueous solvent and stirring to form the nanoparticles coated with the mucoadhesive polymer.

17. The method of claim 16, wherein the concentration of the PLA in the organic solvent is about 1.5 mg/mL to about 12.5 mg/mL, or about 3 mg/mL to about 8.5 mg/mL.

18. The method of claim 16, wherein the concentration of MMF in the organic solvent is about 0.15 mg/mL to about 8.5 mg/mL, about 0.3 mg/mL to about 5 mg/mL, about 0.5 mg/mL to about 3.5 mg/mL, about 0.7 mg/mL to about 2.5 mg/mL, about 0.8 mg/mL to about 1.7 mg/mL or about 1.2 mg/mL.

19. The method of claim 16, wherein the concentration of the mucoadhesive polymer in the surfactant solution is about 4 mg/mL to about 10 mg/mL.

20. The method of claim 16, wherein the conditions to form a nanoparticle solution comprise adding the first solution to the aqueous solution at a rate of about 10 mL/min to about 30 mL/min, about 15 mL/min to about 25 mL/min or about 20 mL/min, followed by vortexing and sonicating.

21. The method of claim 20 wherein the vortexing is for about 5 sec to about 30 sec, about 10 sec to about 20 sec or about 15 sec and the sonicating is for about 1 min to about 10 min, about 3 min to about 8 min or about 5 min.

22. The method of claim 21, wherein the sonicating is done in about 20 sec bursts with about 10 sec rest in between each burst.

23. The method of claim 22, wherein the sonicating is performed at about 40% amplitude using an about ⅛ inch tip size probe.

24. The method of claim 16, wherein the mucoadhesive polymer is dissolved in a dilute acid solution prior to being combined with the surfactant and the concentration of the acid solution is about 1% (v/v) to about 5% (v/v) or about 2% (v/v).

25. The method of claim 16, wherein the surfactant is used as an about 0.1% (w/v) to about 1.0% (w/v) or about 0.5% (w/v) aqueous solution.

26. The method of claim 16, wherein the nanoparticle solution is added to the second solution at a rate of about 10 mL/min to about 30 mL/min, about 15 mL/min to about 25 mL/min or about 20 mL/min followed by stirring for about 1 hour to about 10 hours, about 3 hours to about 8 hours or about 6 hours.

27. The method of claim 16, further comprising collecting the coated nanoparticles from the solution and the coated nanoparticles are suspended in distilled water, a cryoprotectant is added and the nanoparticles are lyophilized.

28. The method of claim 24, wherein the dilute acid solution is dilute acetic acid.

* * * * *

UNITED STATES PATENT AND TRADEMARK OFFICE
CERTIFICATE OF CORRECTION

PATENT NO. : 10,835,489 B2
APPLICATION NO. : 16/291269
DATED : November 17, 2020
INVENTOR(S) : Ellen K. Wasan et al.

It is certified that error appears in the above-identified patent and that said Letters Patent is hereby corrected as shown below:

In the Claims

1. At Column 18, Line 40, Claim 1: "the PLA as a molecular weight (MW)" should read -- the PLA has a molecular weight (MW) --.

Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*